(12) United States Patent
Cantor

(10) Patent No.: US 7,015,005 B2
(45) Date of Patent: *Mar. 21, 2006

(54) METHODS AND DEVICES FOR DETECTING NON-COMPLEXED PROSTATE SPECIFIC ANTIGEN

(75) Inventor: Thomas L. Cantor, El Cajon, CA (US)

(73) Assignee: Scantibodies Laboratory, Inc., Santee, CA (US)

( * ) Notice: Subject to any disclaimer, the term of this patent is extended or adjusted under 35 U.S.C. 154(b) by 567 days.

This patent is subject to a terminal disclaimer.

(21) Appl. No.: 10/108,654

(22) Filed: Mar. 27, 2002

(65) Prior Publication Data

US 2002/0187518 A1 Dec. 12, 2002

Related U.S. Application Data

(63) Continuation of application No. 09/118,844, filed on Jul. 20, 1998, now Pat. No. 6,649,420, which is a continuation-in-part of application No. 08/918,839, filed on Aug. 26, 1997, now Pat. No. 5,994,085.

(51) Int. Cl.
*G02N 33/53* (2006.01)

(52) U.S. Cl. .................. 435/7.21; 435/7.2; 435/7.1; 436/540; 436/536; 436/538; 436/518; 436/529; 436/525

(58) Field of Classification Search ............... 436/540, 436/536, 538, 518, 529, 525; 435/7.1, 7.2, 435/7.21
See application file for complete search history.

(56) References Cited

U.S. PATENT DOCUMENTS

| 5,403,745 A | 4/1995 | Ollington et al. ............. 435/11 |
| 5,710,007 A | 1/1998 | Luderer et al. .............. 435/7.1 |

FOREIGN PATENT DOCUMENTS

| WO | WO 92/01936 | 2/1992 |
| WO | WO 95/18381 | 7/1995 |

OTHER PUBLICATIONS

Luderer et al. "Measurement of the Proportion of Free to Total Prostate-Specific Antigen Improves Diagnositc Performance of Prostate-Specific Antigen in the Diagnostic Gray Zone of Total Prostate-Specific Antigen" Urology 46:187-194 (1995).

Oesterling. "Prostate Specific Antigen: A Critical Assessment of the Most Useful Tumor Marker for Adenocarcinoma of the Prostate" Journal of Urology 145:907-923 (1991).
Oesterling et al, "Influence of Patient Age on the Serum PSA Concentration An Important Clinical Observation" Urologic Clinics Of North America 20(4):671-680 (1993).
Alland et al. "Novel Immuonassay for the Meausrement of Complexed Prostate-Specific Antigen in Serum" Clinical Chemistry 44(6):1216-1223 (1998).
Chichibu et al., Journal of Urology (1996) 155(5):1.
Heeb et al., Biochemistry and Molecular Biology International (1995) 37(5):917-923.
Supplementary European Search Report for EP 98 94 4518, mailed on Sep. 28, 2004, 4 pages.
Wang et al., Clinical Chemistry (1997) 43(Suppl.6):S225.
Wu et al., Journal of Clinical Laboratory Analysis (1995) 9(1):15-24.
Wu et al., Journal of Clinical Laboratory Analysis (1995) 9(1):25-31.

*Primary Examiner*—Sheela J. Huff
(74) *Attorney, Agent, or Firm*—Morrison & Foerster LLP

(57) ABSTRACT

The present invention relates to novel methods and devices for detecting non-complexed prostate specific antigen (PSA), which can be used either alone or in conjunction with total PSA tests to identify patients having either benign prostatic diseases (BPD), such as benign prostatic hyperplasia, prostatitis, or glandular atrophy or prostatic adenocarcinoma (CAP). In a biological sample, one can find not only non-complexed PSA, but also PSA which has formed a complex with $\alpha$1-antichymotrypsin (ACT). The present invention removes or precipitates complexed PSA (PSA-ACT) and ACT from a fluid sample, thereby removing any possible interference due to the binding of complexed PSA to assay reagents. The method requires contacting a biological fluid sample possibly containing a mixture of complexed PSA and non-complexed PSA either with an immunoprecipitating reagent or a device having attached an ACT specific binding partner which in both cases specifically binds only to ACT and the ACT portion of complexed PSA, thereby precipitating ACT and the bound complexed PSA and, thus, leaving any non-complexed PSA unbound and in solution. Then, the sample is measured for non-complexed PSA by means of a conventional specific binding reaction. The device can be a filter having a modified filter media that binds ACT and complexed PSA, while permitting the sample to flow or be pulled through the filter media and into assay reagents. Alternatively, the device can be a removable media that is placed into a sample, allowed to remain long enough to bind any ACT and complexed PSA present, and then withdrawn from the sample prior to running a PSA specific binding assay.

8 Claims, 7 Drawing Sheets

METHODS AND DEVICES FOR DETECTING NON-COMPLEXED PROSTATE SPECIFIC ANTIGEN

RELATED APPLICATION

The present application is a continuation of U.S. patent application Ser. No. 09/118,844, filed Jul. 20, 1998, now U.S. Pat. No. 6,649,420, which is a continuation-in-part of U.S. patent application Ser. No. 08/918,839, filed Aug. 26, 1997, now U.S. Pat. No. 5,994,085. The contents of the above patent and applications are incorporated by reference in their entirety.

TECHNICAL FIELD

The present invention relates to novel methods and devices for detecting non-complexed prostate specific antigen (PSA), which can be used either alone or in conjunction with total PSA tests to identify patients having either benign prostatic diseases (BPD), such as benign prostatic hyperplasia, prostatitis, or glandular atrophy or prostatic adenocarcinoma (CAP). In a biological sample, one can find not only non-complexed PSA, but also PSA which has formed a complex with α1-antichymotrypsin (ACT). The present invention removes or precipitates complexed PSA (PSA-ACT) and ACT from a fluid sample, thereby removing any possible interference due to the binding of complexed PSA to assay reagents. The method requires contacting a biological fluid sample possibly containing a mixture of complexed PSA and non-complexed PSA either with an immunoprecipitating reagent or a device having attached an ACT specific binding partner which in both cases specifically binds only to ACT and the ACT portion of complexed PSA, thereby precipitating ACT and the bound complexed PSA and, thus, leaving any non-complexed PSA unbound and in solution. Then, the sample is measured for non-complexed PSA by means of a conventional specific binding reaction. The device can be a filter having a modified filter media that binds ACT and complexed PSA, while permitting the sample to flow or be pulled through the filter media and into assay reagents. Alternatively, the device can be a removable media that is placed into a sample, allowed to remain long enough to bind any ACT and complexed PSA present, and then withdrawn from the sample prior to running a PSA specific binding assay.

BACKGROUND ART

PSA is recognized as a molecular marker for CAP. Blood or serum based immunoassays measuring the total PSA level have been commercially available for a number of years. However, the detection of total PSA does not necessarily mean that a patient has CAP. In order to distinguish CAP, a total PSA test has to satisfy two elements: a high sensitivity—the ability to detect disease when present, and a high specificity—the ability to detect true negatives and avoid false positives. From clinical experience, total PSA tests have become generally accepted as being predictive of CAP if the total PSA level is greater than 10.0 ng/ml. Total PSA values between 0.0 ng/ml and about 3.9 ng/ml have been considered generally predictive of no disease being present, with a value of about 3.5 ng/ml being used for men under 60 years old and about 2.5 ng/ml being used for men under 50 years old. (See Oesterling, J. E., Cooner, W. H., Jacobsen, S. J., Guess H. A., and Lieber, M. M.: "*Influence of Patient Age on the Serum PSA Concentration and Important Clinical Observations*": Urol. Clin. North Am.; Vol. 20: 671–680, 1993.)

PSA is primarily organ-specific, not cancer specific. Thus, PSA in blood or serum can result not only from CAP, but also from normal or hyperplastic prostate tissues. Historically, a total PSA test cannot reliably distinguish BPD from CAP at less than 10.0 ng/ml. Studies have found that 43% (136/319) of patients with organ-confined CAP have a total PSA value within the normal range of less than 4.0 ng/ml. Moreover, about 25% (148/597) of men with BPD have a total PSA value above 4.0 ng/ml. (See Oesterling, J. E.: "*Prostate Specific Antigen: A Critical Assessment of the Most Useful Tumor Marker for Adenocarcinoma of the Prostate*", J. Urol., Vol: 145: 907–923, 1991.) Standard medical practice is to biopsy patients over 60 years old having total PSA levels of between 4.0 ng/ml and 10.0 ng/ml because about 30% of those patients have CAP. Likewise, patients between 50 years and 60 years old whose total PSA falls between 3.5 ng/ml and 10.0 ng/ml and patients under 50 years old whose total PSA falls between 2.5 ng/ml and 10.0 ng/ml are also biopsied under current medical practice.

One method for detecting CAP is disclosed in U.S. Pat. No. 5,501,983 to Hans Lilja et alia. In general, the Lilja patent discloses using immunoassays to measure "free PSA" and a complexed form of PSA. "Free PSA" is a 33 kDa single chain glycoenzyme that is produced by the epithelial cells lining the acini and prostatic ducts of the prostate gland. Complexed PSA refers primarily to a 90 kDa complex of PSA bound to α1-antichymotrypsin (ACT) protein. Free PSA and complexed PSA, and their proportions are applied in the diagnosis of patients with CAP. Throughout, the specification discloses using a combination of a free PSA to total PSA (F/T) proportion and a complexed PSA to total PSA (C/T) proportion for use in diagnosing CAP. No prostate needle biopsy were performed on the patients, and the patients covered a full range of total PSA values. The text provides no guidance as to specifically how one uses these proportions.

A significant advance in diagnosing BPD in a male human patient without requiring a biopsy is disclosed by Luderer, A. A., et alia in "*Measurement of the Proportion of Free to Total Prostate-Specific Antigen Improves Diagnostic Performance of Prostate-Specific Antigen in The Diagnostic Gray Zone of Total Prostate-Specific Antigen*", Urol., Vol. 46: 187–194, 1995. This reflex method eliminates the need for about one-third of those patients to undergo such a biopsy. For those patients in the gray diagnostic zone, the method comprises four steps. First, one measures the total PSA level in the blood or serum of the patient. Second, one measures the free PSA level in the blood or serum of a patient, but only if he has a total PSA level of between about 2.5 ng/ml and about 10.0 ng/ml. If the patient has a total PSA level below 2.5 ng/ml, then he is diagnosed to have BPD. If the patient has a total PSA level above 10.0 ng/ml, then he is presumed to have CAP and must be biopsied. Third, one calculates the proportion of free PSA to total PSA. Fourth and finally, one diagnoses the patient as having BPD if the calculated proportion of free PSA to total PSA is equal to or greater than about 25%.

Another method for detecting complexed PSA has been proposed by Yeung, K. K., et alia, in "*Novel Immunoassay for the Measurement of Complexed Prostate-Specific Antigen in Serum*", Clin. Chem., Vol. 44:1216–1223, 1998. In this assay an antibody is used to bind to a particular epitope, rendering a potential assay interferent unable to be detected by immunoassay antibodies. In particular, antibodies specific for the region on PSA where ACT binds to PSA are used to change the conformation of non-complexed PSA, thereby rendering the non-complexed PSA unable to be detected by immunoassay antibodies that can bind only to complexed PSA. Only antibodies which cause the desired conformational change will work.

The removal of an unwanted component from a biological sample is disclosed in U.S. Pat. No. 5,403,745 to James F. Ollington et alia. When assaying for a cholesterol analyte in a targeted lipoprotein class, there can be present in a sample at least one cholesterol-containing interfering substance in another lipoprotein class. This interfering substance is removed by binding the interfering substance with immobilized antibodies.

DISCLOSURE OF THE INVENTION

The present invention relates to a method for detecting non-complexed PSA in a biological sample using an assay that incorporates a specific binding reaction. For the purposes of this invention, a distinction is made between "free PSA" and "non-complexed PSA". "Free PSA" is defined as the form of PSA that is measured by antibodies disclosed by Lilja, namely, those which will normally recognize an epitope on PSA when PSA is not complexed with ACT, but will not recognize that same epitope if the PSA is complexed with ACT. "Non-complexed PSA" is the PSA moiety which remains after all ACT moiety in a mixture of free PSA and complexed PSA has been specifically bound by an antibody and removed or precipitated. The distinction between the two is important. In some cases, the Lilja method can detect as free PSA what is really complexed PSA. This erroneous detection occurs because in some samples the ACT binding epitopes on PSA are revealed due to conformational changes induced perhaps by sample specific interferents. The free PSA antibody can now detect the PSA portion of the complexed PSA. This over recovery of signal for free PSA is significant in that the difference in the distribution of free PSA values and total PSA values has already been shown by Luderer to be resolvable into distinct patient populations for CAP and BPD. A true measurement for non-complexed PSA without over recovery can enhance the resolving power of such assays, and thereby improve the diagnostic utility of PSA measurements in CAP diagnostics.

The present invention removes complexed PSA from further participation in a specific binding reaction, thereby removing any possible interference due to the binding of complexed PSA in an immunoassay for free PSA. An added advantage of the present invention is that the present method will measure non-complexed PSA while working with measurement antibodies that typically are used to measure either total PSA or free PSA, unlike either the Lilja or Yeung methods which require specific measurement antibodies to measure free PSA and complexed PSA, respectively. In particular, the present invention involves either treating a fluid sample with a device so as to remove physically complexed PSA from the solution or treating a fluid sample with an immuno-precipitating reagent so as to form an insoluble complex which contains either any ACT or any complexed PSA present in the sample before measuring for non-complexed PSA by means of an immunoassay. One should note that the addition of the immuno-precipitating reagent can occur either before the measurement immunoassay components are added to the sample, or along with these components. In a preferred embodiment, the immuno-precipitating reagent can be part of the sample diluent component used for generating a measurement signal. Also, if one physically separates the precipitate from the sample, then conventional techniques can be used, such as washing, filtration, fluid transfer, and centrifugation.

In the case of forming the insoluble complex, a specific binding immuno-precipitating reagent is added to a sample in a solution in an amount sufficient to bind and precipitate any ACT present in the sample, including PSA-ACT complex and ACT not complexed with PSA. The immuno-precipitating reagent binds to the ACT portion of the PSA-ACT complex but not to non-complexed PSA. The combination of PSA-ACT complex and the immuno-precipitating reagent is not able to bind to an antibody that recognizes the PSA portion of the PSA-ACT complex for measurement by an immunoassay. Most importantly, the combination of either PSA-ACT complex or ACT and immuno-precipitating reagent is of a sufficient mass to precipitate out of solution. (For the purposes of the present invention, "precipitate" includes any physical or chemical process whereby PSA-ACT complex is transported from a dissolved state, (i.e., in solution), to an out of solution state that precludes participation in a specific binding reaction involving antibodies.) Typically the immuno-precipitating reagent is an anti-ACT antibody.

The present invention also includes using a multiple component immuno-precipitating reagent. For example, the immuno-precipitating reagent can be comprised of two specific binding reagents. A first specific binding reagent binds to the ACT portion of the PSA-ACT complex but does not have a sufficient mass when bound thereto to precipitate the combination from the sample. A second specific binding reagent binds to the bound first specific binding reagent, wherein the combined mass of the PSA-ACT complex and the two specific binding reagents is sufficient to form a precipitate. Neither of these specific binding partners interferes or binds to non-complexed PSA. Such antibodies are commercially available from Scantibodies Laboratory, Inc. of Santee, Calif. USA. For example, a goat anti-ACT antibody can be used for the first specific binding partner, and a rabbit anti-goat antibody can be used for the second specific binding partner. The fluid sample is kept in contact with the second specific binding partner for a time and under conditions sufficient to bind all of the ACT and complexed PSA which is bound to the first specific binding partner, which are known to those of skill in the art.

When using a pretreatment device, the method comprises four steps. First, one contacts a biological fluid sample containing a mixture of complexed PSA and non-complexed PSA with a pretreatment device. The pretreatment device has attached to its surfaces an excess of at least one specific binding partner which specifically binds only to the ACT portion of complexed PSA and to ACT, but not to non-complexed PSA, leaving any non-complexed PSA unbound. Next, one keeps the fluid sample in contact with the pretreatment device for a time sufficient to bind all complexed PSA to any attached specific binding partners. Thirdly, one separates the fluid sample and the device. The fluid sample is exposed to conventional specific binding assay reagents for detecting PSA under conditions which permit a measurement of PSA. Finally, one measures the amount of PSA present in the fluid sample, which is non-complexed. Again, the present method will work with measurement antibodies that measure either total PSA or free PSA.

In one embodiment, a pretreatment device comprises two main elements. The first is a filter that has a modified filter media. The filter is dimensioned and configured so as to permit the fluid sample to flow or be pulled through the filter media and into a vessel containing assay reagents. Suitable filter devices are commercially available. The second element is that the modified filter media has attached to the surface thereof at least one specific binding partner which specifically binds only to the ACT portion of complexed PSA and to ACT, but not to non-complexed PSA, leaving any non-complexed PSA unbound. The modified media has sufficient specific binding partner present to bind all ACT present in the sample, whether bound or otherwise.

In an alternative embodiment, the pretreatment device comprises a removable media or solid support having at least one specific binding partner attached to the surface which specifically binds only to the ACT portion of complexed PSA and to ACT, but not to non-complexed PSA, leaving any non-complexed PSA unbound. The removable media can be conventional assay type media such as beads or strips. The removable media is dimensioned and configured so as to be placed into and withdrawn from the fluid sample, which has been placed in a vessel.

In yet another alternative embodiment, the pretreatment device comprises a fluid sample vessel having the specific binding partners described above attached to the surface. The sample is placed within the vessel.

BEST MODES FOR CARRYING OUT THE INVENTION

PSA Assay

Figure 1:
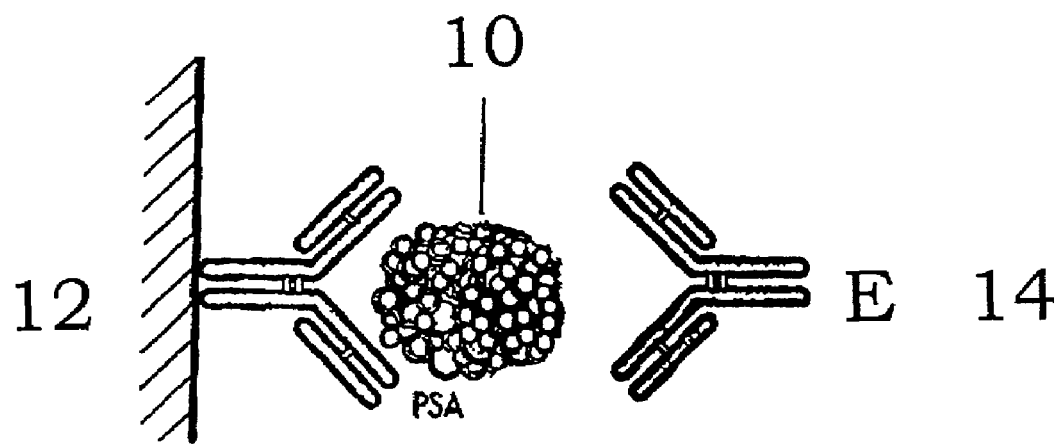
FIG. 1 is a diagrammatic view of an immunoassay for PSA.

In preferred embodiments described below, the present method comprises measuring non-complexed PSA using any specific binding assay that measures either total PSA or free PSA. Suitable PSA assays include a sandwich monoclonal/monoclonal immunoassay manufactured by Tosoh Medics, Inc. (Tosoh) of Foster City, Calif. USA for total PSA, one made by Hybritech, Inc. of San Diego, Calif. USA for free PSA, or one made by CIS-Bio of Saclay, France for free PSA. FIG. 1 shows diagrammatically how, in the final configuration in a traditional use, this assay captures PSA (10) using a capture antibody (12) and detects PSA using a labeled antibody (14).

Pretreatment Filter Device

Figure 2:
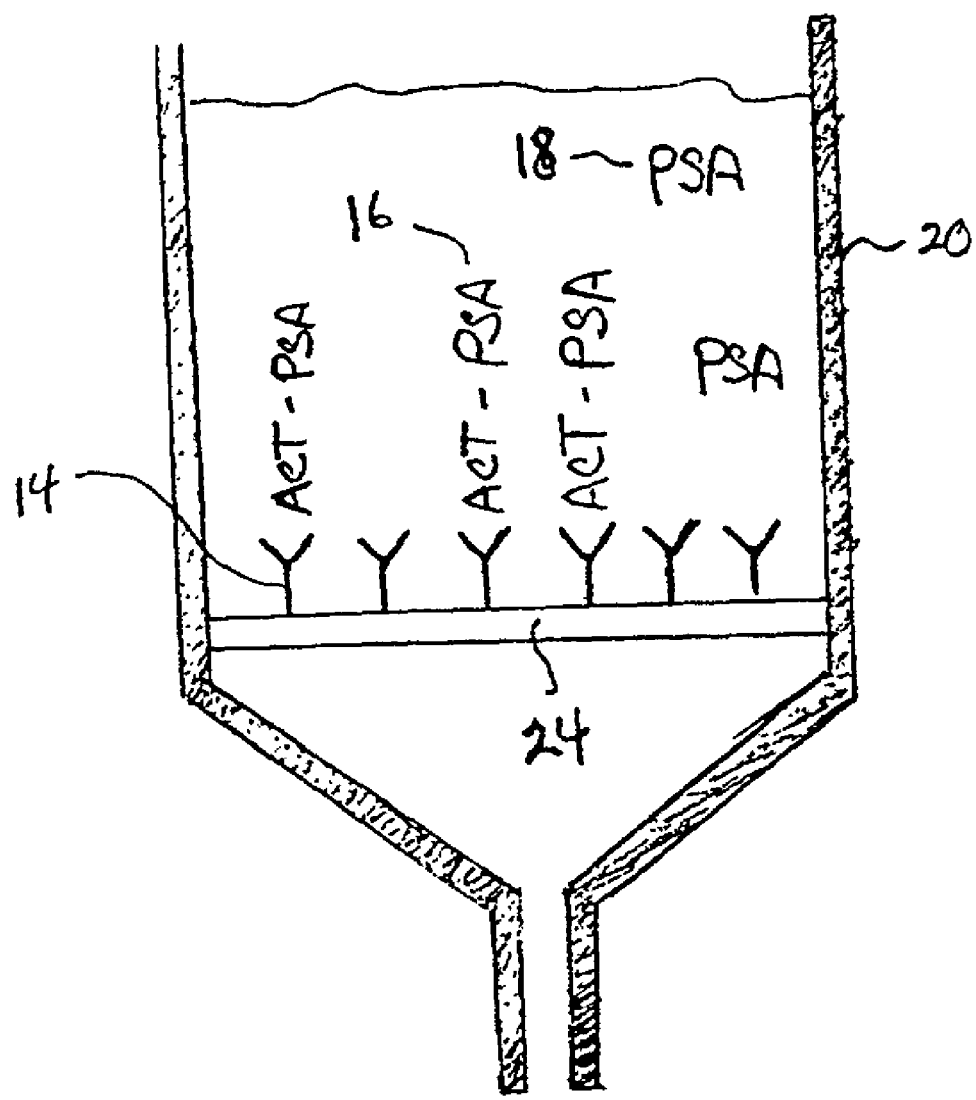
FIG. 2 is a sectional view of a pretreatment filter device in accordance with the present invention.

As shown in FIG. 2, a pretreatment filter device comprises a vessel (20) into which the fluid sample can be placed either by pouring, pipetting, or other conventional means for transferring fluids. One wall or surface of the vessel has an opening (22) for allowing the fluid sample to be removed from the pretreatment device by flowing or being pulled by vacuum downward through the opening. Disposed within and about the opening is a filter media (24) such as cellulose. Attached to the surface of the filter media are a plurality of antibodies (14) which are specific in binding ACT, either alone or complexed with PSA (16) but not non-complexed PSA (18). Suitable antibodies include goat anti-ACT, which are available from Scantibodies Laboratory, Inc. of Santee, Calif. USA.

These antibodies can be bound by conventional techniques known to those of skill in the art. The filter media may be a bibulous material capable of drawing fluid sample into the media by capillary action. The volume of bibulous material present is sufficient to attach the excess of antibodies. Suitable bibulous materials include blotting papers, filter papers, non-woven natural polymers, and non-woven synthetic polymers. The dimensions of the materials will vary depending upon sample size and absorptive capacity, as known to those of ordinary skill in the art.

Removable Pretreatment Device

Figure 3:
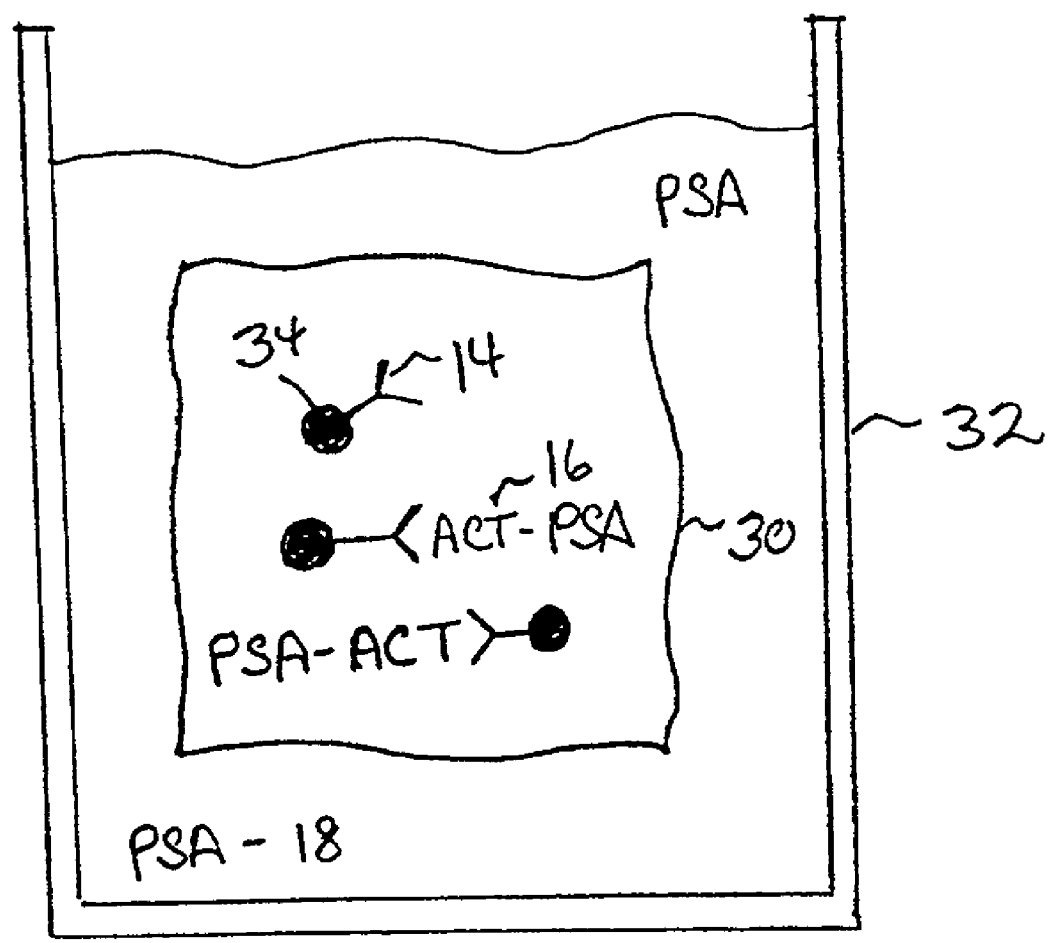
FIG. 3 is a sectional view of a removable pretreatment device in accordance with the present invention.

As shown in FIG. 3, a removable pretreatment device can take the form of a disposable bead pack (30) which may be placed into a container or vessel (32) either before or after placing a fluid sample into the vessel. The pack contains a plurality of beads (34) such as are used in existing immunoassay devices. Suitable bead materials include polystyrene or latex. Attached to the surface of the beads are an excess of antibodies (14) specific to ACT and the ACT portion of complexed PSA. Suitable antibodies include goat anti-ACT, which are available from Scantibodies Laboratory, Inc. of Santee, Calif. USA. These antibodies can be bound by conventional techniques known to those of skill in the art.

The pretreatment device is placed into the sample for a time and under conditions sufficient to allow any complexed PSA present to bind to the antibodies (14). Only non-complexed PSA (18) remains unbound in the fluid sample. The pack may either be withdrawn from the fluid sample and thrown away, left in place, or the sample may be removed leaving the pack in the vessel. Alternatively, a pretreatment device can be in the form of a coated dipstick or a disposable piece of coated media such as cellulose, nitrocellulose, glass fibers, and the like. One measures for non-complexed PSA using conventional immunoassays for either total PSA or free PSA.

Coated Tube Pretreatment Device

Figure 4:
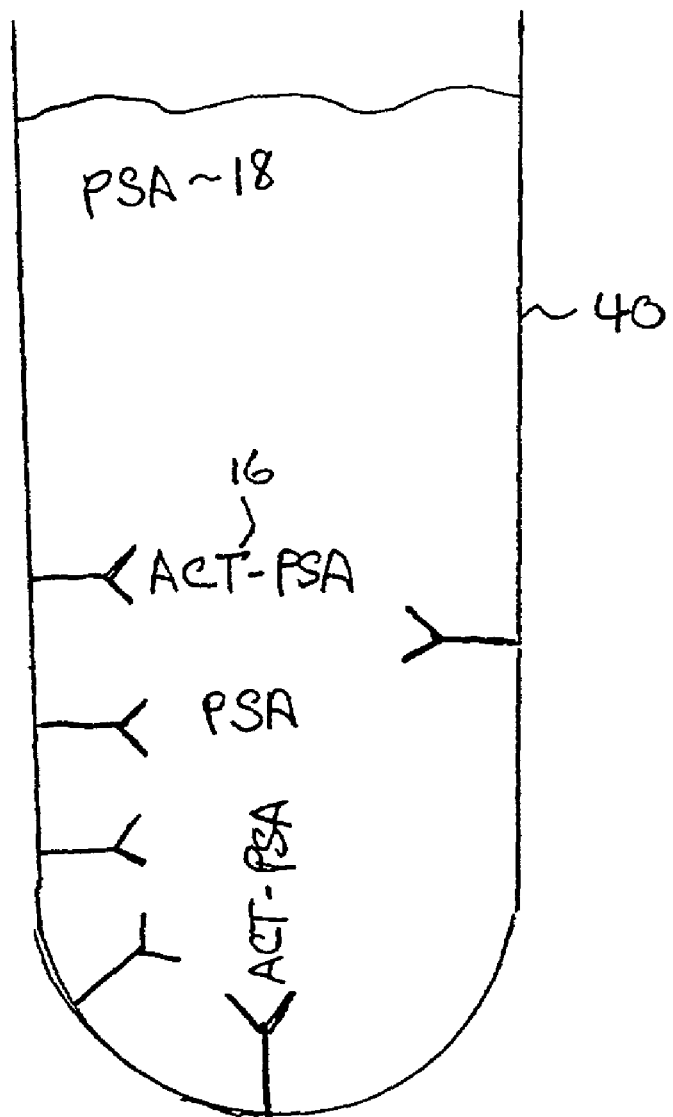
FIG. 4 is a sectional view of a coated tube pretreatment device in accordance with the present invention.

As shown in FIG. 4, a coated tube pretreatment device comprises a vessel (40) having disposed or deposited on the interior surfaces (42) an excess of anti-ACT antibodies (14). Suitable antibodies include goat anti-ACT, which are available from Scantibodies Laboratory, Inc. of Santee, Calif. USA. These antibodies can be bound by conventional techniques known to those of skill in the art.

In use, ACT and complexed PSA (16) will bind to the anti-ACT antibodies, leaving non-complexed PSA (18) in the solution. One measures for non-complexed PSA using conventional immunoassays for either total PSA or free PSA.

Immuno-Precipitating Reagent Method

Figure 5:
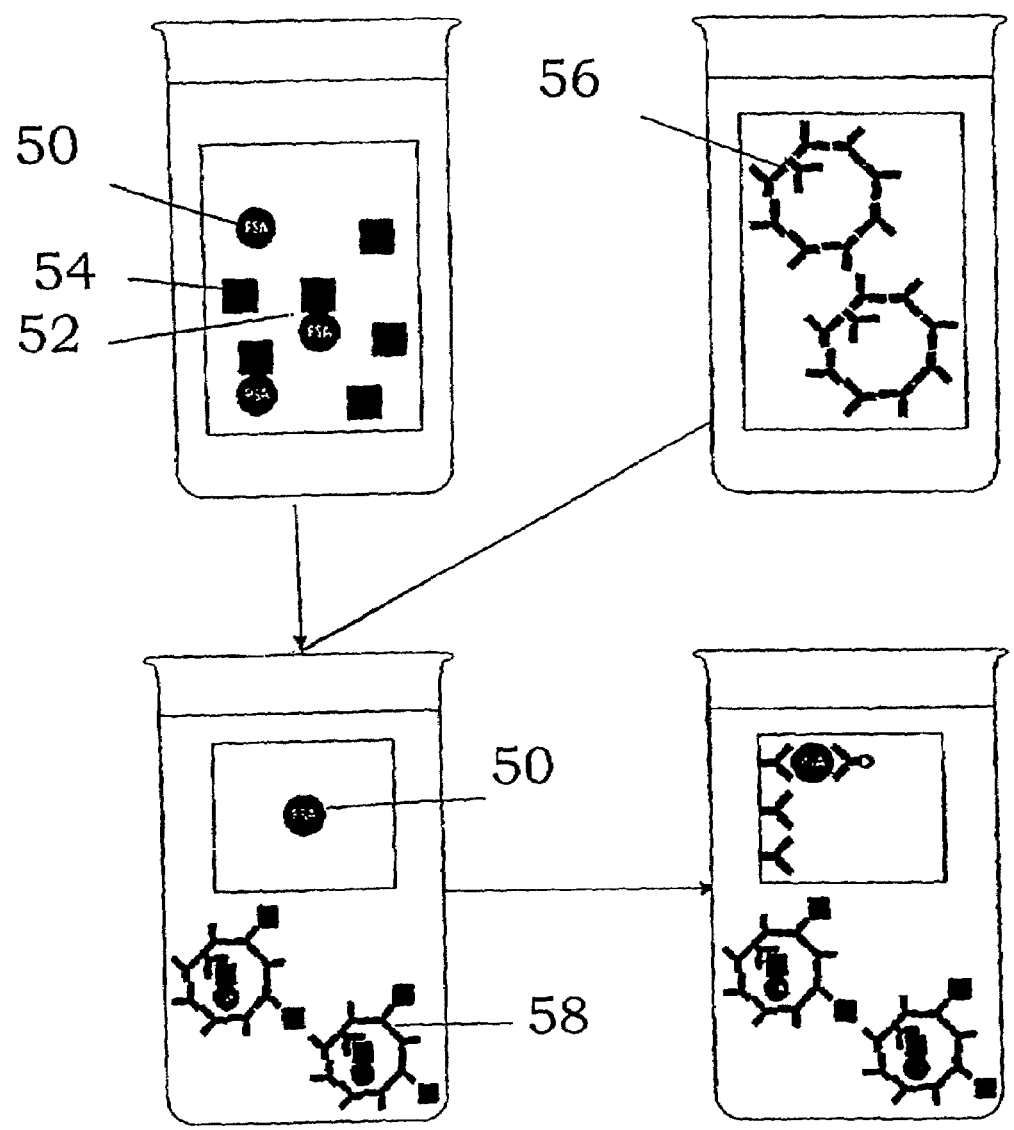
FIG. 5 is a diagrammatic view of an embodiment of the present invention wherein a precipitate is formed.

As shown in FIG. 5, a fluid sample from a male human patient that contains non-complexed PSA (50), complexed PSA (52), and free ACT (54) is placed in a vessel. Typical sample sizes range from 25 µl to 5 ml. Immuno-precipitating reagent (56) is added to the sample, 25 µl to 5 ml of a goat anti-ACT commercially available from Scantibodies Laboratory, Inc. of Santee, Calif., USA. This amount is sufficient to bind and precipitate the ACT present in the sample (58), either bound to PSA or not. The immuno-precipitating reagent is allowed to remain in contact with the sample for about one to five minutes. Non-complexed PSA is measured by a number of commercially available immunoassays for either total PSA or free PSA.

Measurement of Non-Complexed PSA by Total PSA Immunoassay

Figure 6:
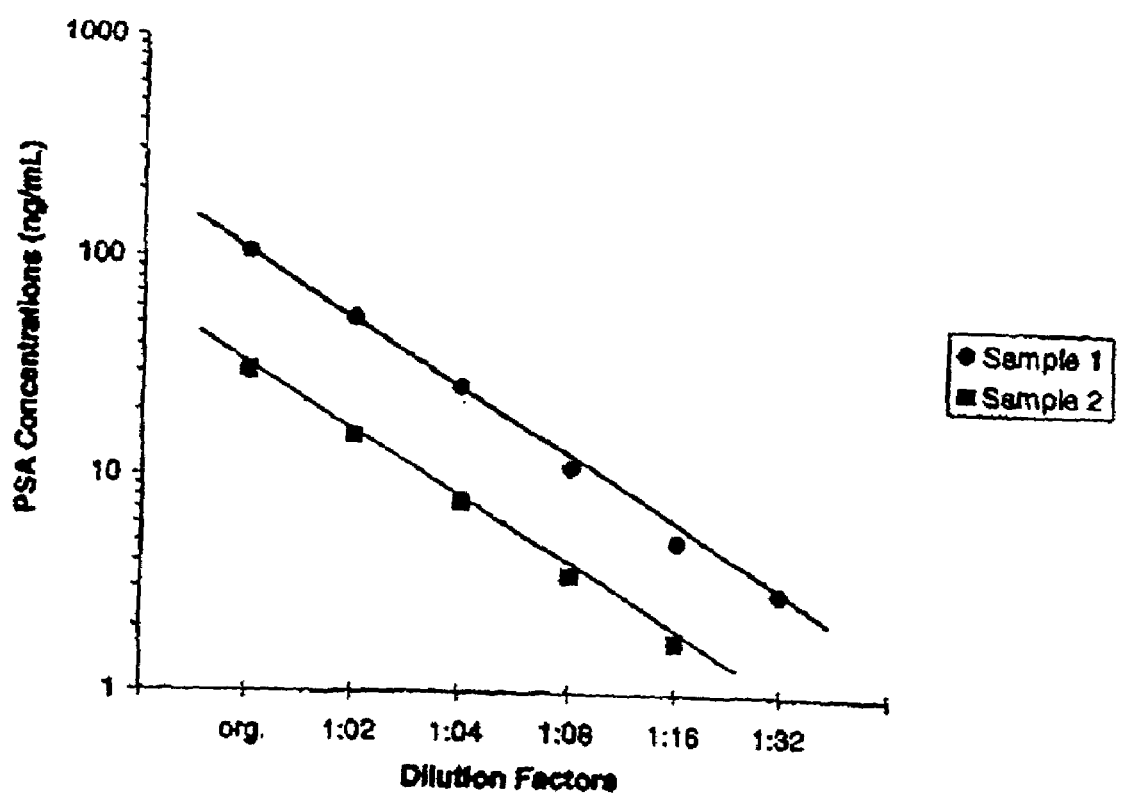
FIG. 6 is a graph showing the serial dilution of patient samples using the present invention to measure non-complexed PSA.

Using the above pretreatment method, non-complexed PSA was measured using a total PSA immunoassay from Scantibodies Laboratory, Inc. of Santee, Calif., USA. More particularly, 25 microliters of patient sample was pipetted into a plastic 12 mm by 75 mm tube. One ¼ inch polystyrene bead coated with a monoclonal antibody to PSA, (a capture antibody), was added to each tube. Finally, 200 microliters of biotinylated goat anti-PSA was added to each tube. The tube was incubated for two hours at room temperature (18 to 28 degrees C.). The bead and tube were washed and liquid was removed from the tube containing the bead. To the tube was added 200 microliters of horseradish peroxidase conjugated streptavidin, which were allowed to incubate for 30 minutes. The tube and bead were washed, and all liquid was removed. To develop a signal, 200 microliters of substrate (ortho-phenylenediamine) was added to each tube. The concentration of PSA present, non-complexed PSA, was correlated with calibrators to the change in color, which was quantitated spectrophotometrically. FIG. 6 shows the sample dilution linearity for this method. Two samples were diluted and tested using the pretreatment and being measured for non-complexed PSA by means of the Scantibodies Laboratory total PSA assay.

Using the above pretreatment method, non-complexed PSA is measured using a total PSA immunoassay from Tosoh. The manufacturer's instructions were followed for the assay of total PSA using their AIA test method. For the generation of the non-complexed PSA results using the Tosoh total PSA assay, 100 microliters of patient sera was incubated at room temperature with 100 microliters of Scantibodies Laboratory, Inc. goat anti-ACT for one hour. The mixture was treated as a normal patient sample and assayed in accordance with the instructions for assaying total PSA by the AIA system, albeit non-complexed PSA results were obtained.

Measurement of Free PSA

For comparative purposes, free PSA is measured using a free PSA immunoassay from CIS-Bio of Saclay, France. The manufacturer's instructions were followed for the assay of free PSA using the disclosed IRMA test methods.

Comparison of Measurement Methods

Figure 7:
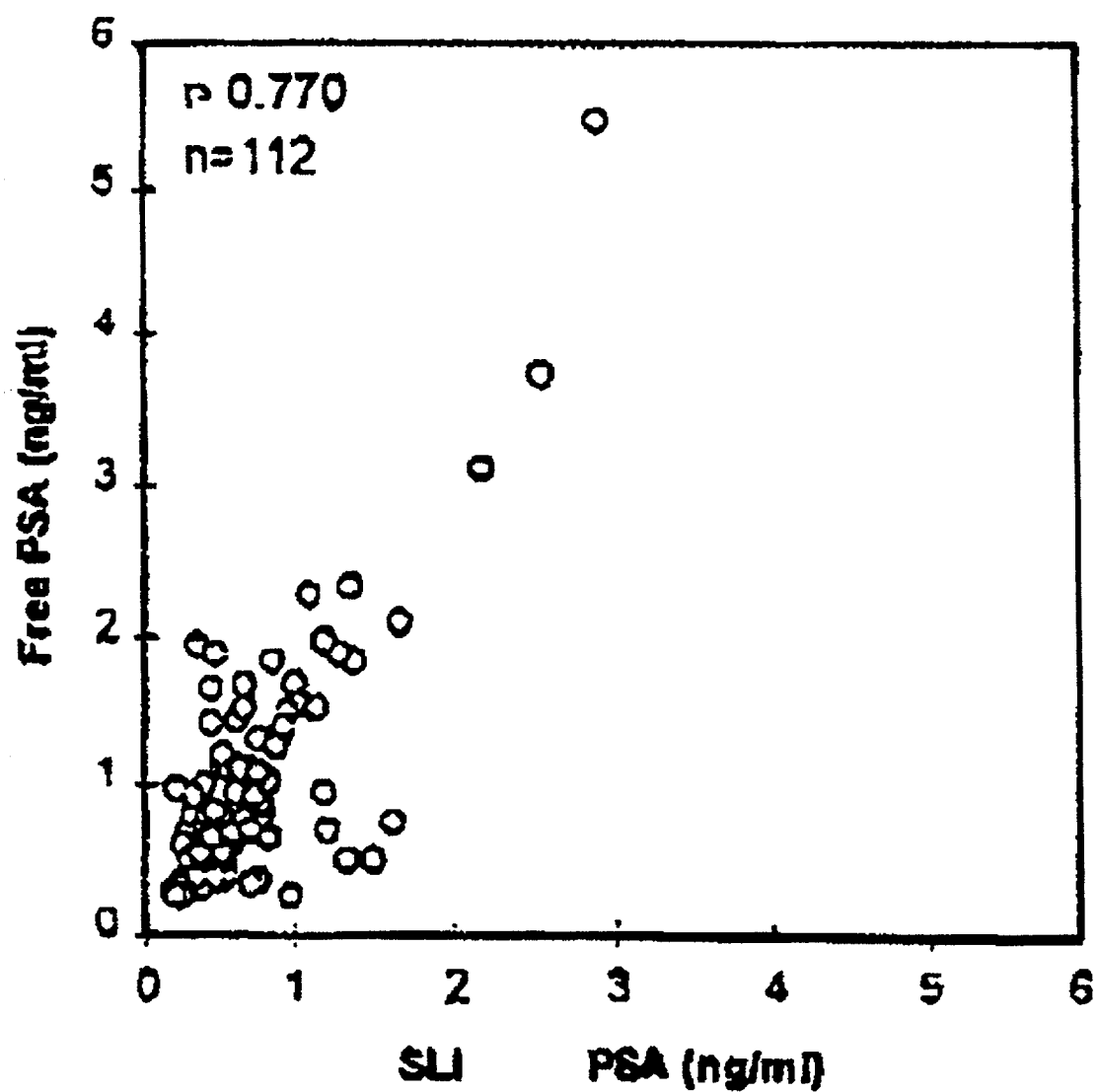
FIG. 7 is a graph showing the correlation between results achieved testing samples from 63 patients with the present invention versus the Lilja free PSA method.

The following table compares results obtained for 63 patient samples measured for free PSA (CIS-Bio free PSA immunoassay), non-complexed PSA (Tosoh Medics total PSA immunoassay and Scantibodies Laboratory, Inc. immuno-precipitating reagent), and total PSA (Tosoh Medics total PSA immunoassay) as described above. All values are in ng/ml. (FIG. 7 is a graph showing the correlation between results achieved testing samples from 63 patients with the present invention versus the Lilja free PSA method.)

| FREE PSA | NON-COMPLEXED PSA | TOTAL PSA |
|---|---|---|
| <0.1 | <0.1 | <0.1 |
| <0.1 | <0.1 | <0.1 |
| <0.1 | <0.1 | <0.1 |
| <0.1 | <0.1 | <0.1 |
| <0.1 | <0.1 | <0.1 |
| <0.1 | <0.1 | <0.1 |
| <0.1 | <0.1 | <0.1 |
| 0.1 | 0.2 | 0.1 |
| 0.1 | 0.2 | 0.1 |
| 0.2 | <0.1 | 0.2 |
| 0.2 | <0.1 | 0.3 |
| 0.2 | 0.1 | 0.3 |
| 0.3 | 0.2 | 0.3 |
| 0.3 | 0.3 | 0.3 |
| 0.2 | <0.1 | 0.4 |
| 0.2 | 0.2 | 0.4 |
| 0.3 | 0.2 | 0.4 |
| 0.3 | 0.2 | 0.4 |
| 0.2 | 0.2 | 0.4 |
| 0.2 | 0.2 | 0.5 |
| 0.4 | 0.2 | 0.5 |
| <0.1 | <0.1 | 0.6 |
| 0.2 | 0.1 | 0.6 |
| 0.1 | <0.1 | 0.7 |
| 0.2 | <0.1 | 0.7 |
| 0.2 | 0.2 | 0.7 |
| 0.5 | 0.4 | 0.8 |
| 0.5 | 0.4 | 0.8 |
| 0.6 | 0.5 | 0.9 |
| 0.3 | 0.1 | 1.0 |
| 0.4 | 0.3 | 1.0 |
| 0.5 | 0.1 | 1.1 |
| 0.5 | 0.5 | 1.2 |
| 0.5 | 0.3 | 1.3 |
| 0.6 | 0.6 | 1.3 |
| 0.3 | 0.2 | 1.4 |
| 0.4 | 0.1 | 1.5 |
| 0.8 | 0.7 | 1.8 |
| 0.7 | 0.5 | 2.1 |
| 1.1 | 0.9 | 2.1 |
| 0.2 | <0.1 | 2.3 |
| 0.5 | 0.4 | 2.3 |
| 0.8 | 0.8 | 2.4 |
| 0.8 | 0.8 | 2.6 |
| 0.8 | 0.9 | 2.7 |
| 0.8 | 0.6 | 3.0 |
| 0.6 | 0.5 | 3.1 |
| 0.5 | 0.5 | 3.3 |
| 1.0 | 1.0 | 3.5 |
| 2.3 | 2.1 | 3.6 |
| 0.5 | 0.3 | 3.8 |
| 0.8 | 0.7 | 3.8 |
| 2.1 | 1.8 | 3.8 |
| 1.8 | 1.8 | 3.8 |
| 2.1 | 1.9 | 3.8 |
| 0.3 | 0.4 | 4.7 |
| 0.8 | 0.8 | 4.8 |
| 2.4 | 2.3 | 5.6 |
| 0.8 | 0.8 | 5.9 |
| 1.5 | 1.6 | 6.4 |
| 2.1 | 1.2* | 7.7 |
| 2.2 | 2.0 | 8.4 |
| 0.6 | 0.7 | 11.9 |

*-This sample is believed to be an example of where an over-recovery has occurred using the Lilja free PSA method.

The ordinarily skilled artisan can appreciate that the present invention can incorporate any number of the preferred features described above.

All publications or unpublished patent applications mentioned herein are hereby incorporated by reference thereto.

Other embodiments of the present invention are not presented here which are obvious to those of ordinary skill in the art, now or during the term of any patent issuing from this patent specification, and thus, are within the spirit and scope of the present invention.

I claim:

1. A method for measuring the amount of non-complexed prostate specific antigen (PSA) in a sample from a male human patient comprising:
   a) adding a specific binding immuno-precipitating reagent to said sample in a solution in an amount sufficient to bind and precipitate any α1-antichymotrypsin (ACT) present in the sample, whether complexed with PSA (PSA-ACT complex) or not; wherein the immuno-precipitating reagent binds either to the ACT or the ACT portion of the PSA-ACT complex but not to non complexed PSA, and the combination of either ACT or PSA-ACT complex and the immuno-precipitating reagent is of a sufficient mass to precipitate out of solution; and
   b) measuring the amount of non-complexed PSA, which remains in solution, by using an antibody that recognizes PSA in a specific binding reaction,
   wherein the immuno-precipitating reagent is added to the solution as part of an assay component for measuring non-complexed PSA.

2. The method of claim 1, wherein the immuno-precipitating reagent is comprised of two specific binding reagents; a first specific binding reagent that binds to the ACT portion of the PSA-ACT complex and ACT but does not have a sufficient mass when bound thereto to cause either PSA-ACT complex or ACT to precipitate from the sample, and a second specific binding reagent that binds to the first specific binding reagent wherein the combined mass of either ACT or the PSA-ACT complex and the two specific binding reagents is sufficient to form a precipitate.

3. A method for measuring the amount of non-complexed prostate specific antigen (PSA) in a sample from a male human patient comprising:
   a) adding a specific binding immuno-precipitating reagent to said sample in a solution in an amount sufficient to bind and precipitate any α1-antichymotrypsin (ACT) present in the sample, whether complexed with prostate specific antigen (PSA-ACT complex) or not; wherein the immuno-precipitating reagent binds either to the ACT or the ACT portion of the PSA-ACT complex but not to non complexed PSA, and the combination of either ACT or PSA-ACT complex and the immuno-precipitating reagent is of a sufficient mass to precipitate out of solution; and
   b) measuring the amount of non-complexed PSA, which remains in solution, by using an antibody that recognizes PSA in a specific binding reaction, and
   wherein the immuno-precipitating reagent is added before the measurement of the non-complexed PSA is completed.

4. The method of claim 3, wherein the immuno-precipitating reagent is comprised of two specific binding reagents; a first specific binding reagent that binds to the ACT portion of the PSA-ACT complex and ACT but does not have a sufficient mass when bound thereto to cause either PSA-ACT complex or ACT to precipitate from the sample, and a second specific binding reagent that binds to the first specific binding reagent wherein the combined mass of either ACT or the PSA-ACT complex and the two specific binding reagents is sufficient to form a precipitate.

5. The method of claim 3, wherein the immuno-precipitating reagent is added before an immunoassay component for measuring the amount of non-complexed PSA is added.

6. The method of claim 3, wherein the immuno-precipitating reagent is added along with an immunoassay component for measuring the amount of non-complexed PSA.

7. The method of claim 4, wherein the immuno-precipitating reagent is added before an immunoassay component for measuring the amount of non-complexed PSA is added.

8. The method of claim 4, wherein the immuno-precipitating reagent is added along with an immunoassay component for measuring the amount of non-complexed PSA.

* * * * *